US010111898B2

(12) United States Patent
Primiano et al.

(10) Patent No.: US 10,111,898 B2
(45) Date of Patent: Oct. 30, 2018

(54) ANTI-TUMOR COMPOSITIONS AND METHODS

(71) Applicant: PeptiMed, Inc., Madison, WI (US)

(72) Inventors: Thomas Primiano, Monona, WI (US); Bey-Dih Chang, Madison, WI (US)

(73) Assignee: PeptiMed, Inc., Madison, WI (US)

( * ) Notice: Subject to any disclaimer, the term of this patent is extended or adjusted under 35 U.S.C. 154(b) by 0 days.

(21) Appl. No.: 14/740,079

(22) Filed: Jun. 15, 2015

(65) Prior Publication Data
US 2016/0058784 A1 Mar. 3, 2016

Related U.S. Application Data

(60) Provisional application No. 62/070,495, filed on Aug. 27, 2014.

(51) Int. Cl.
C07H 21/02 (2006.01)
C07H 21/04 (2006.01)
A61K 48/00 (2006.01)
A61K 31/713 (2006.01)
C12N 15/117 (2010.01)
A61K 9/127 (2006.01)
A61K 45/06 (2006.01)
A61K 47/64 (2017.01)
A61K 47/69 (2017.01)

(52) U.S. Cl.
CPC ............ A61K 31/713 (2013.01); A61K 9/127 (2013.01); A61K 9/1271 (2013.01); A61K 45/06 (2013.01); A61K 47/646 (2017.08); A61K 47/6935 (2017.08); C12N 15/117 (2013.01); C12N 2310/17 (2013.01); C12N 2310/351 (2013.01)

(58) Field of Classification Search
CPC .. C12N 15/113; C12N 2310/11; A61K 31/713
See application file for complete search history.

(56) References Cited

U.S. PATENT DOCUMENTS

| 3,773,919 | A | 11/1973 | Albert et al. | |
|---|---|---|---|---|
| 5,151,510 | A | 9/1992 | Stec et al. | |
| 6,395,713 | B1 | 5/2002 | Beigelman et al. | |
| 8,680,045 | B2 | 3/2014 | Primiano et al. | |
| 2010/0196350 | A1* | 8/2010 | Hong ................ | C07K 16/2803 424/130.1 |
| 2011/0245230 | A1* | 10/2011 | Mitchell ............. | C07D 239/70 514/210.21 |
| 2011/0257244 | A1* | 10/2011 | Manoharan .......... | C12N 15/113 514/44 A |
| 2015/0038549 | A1* | 2/2015 | Smith ................. | C12N 15/111 514/44 A |

FOREIGN PATENT DOCUMENTS

| EP | 0036676 | 9/1981 |
|---|---|---|
| EP | 0058481 | 8/1982 |
| EP | 0088046 | 9/1983 |
| EP | 0143949 | 3/1985 |
| WO | WO1993015722 | 8/1993 |
| WO | WO199402595 | 2/1994 |
| WO | WO199904819 | 2/1999 |
| WO | WO199905094 | 2/1999 |
| WO | WO200053722 | 9/2000 |
| WO | 2012/061443 A2 | 5/2012 |

OTHER PUBLICATIONS

Alexopoulou et al., "Recognition of double-stranded RNA and activation of NF-kappaB by Toll-like receptor 3." Nature 413(6857): 732-738. (2001).
Bridge et al., "Induction of an interferon response by RNAi vectors in mammalian cells." Nat Genet 34(3): 263-264. (2003).
Cekaite et al., "Gene expression analysis in blood cells in response tounmodified and 2'-modified siRNAs reveals TLR-dependent and independenteffects." J Mol Biol 365(1): 90-108. (2007).
Christensen et al., ""Toll-like receptor 7 and TLR9 dictate autoantibody specificity and have opposing inflammatory and regulatory roles in amurine model of lupus."" Immunity 25(3): 417-428. (2006).
Diebold et al, "Innate antiviral responses by means of TLR7-mediated recognition of single-stranded RNA." Science 303(5663): 1529-1531. (2004).
Dryden et al., The lack of specificity of neuropeptide Y (NPY) antisense oligodeoxynucleotides administered intracerebroventricularly in inhibiting food intake and NPY gene expression in the rat hypothalamus, J Endocrinology, 157(1): 169-175. (Apr. 1998).
Elbashir et al. "Duplexes of 21-nucleotide RNAs mediate RNA interference in cultured mammalian cells." Nature 411(6836): 494-498. (2001).
Fire et al., "Potent and specific genetic interference by double-strandedRNA in Caenorhabditis elegans." Nature 391(6669): 806-811. (1998).
Heil et al., ."Species-specific recognition of single-stranded RNA viatoll-like receptor 7 and 8." Science 303(5663): 1526-1529. (2004).
Hornung et al., "Sequence-specific potent induction of IFNalpha by short interfering RNA in plasmacytoid dendritic cells through TLR7." NatMed 11(3): 263-270. (2005).
Huber et al., "NF-kappaB is essential for epithelial-mesenchymal transition and metastasis in a model of breast cancer progression.", J Clin Invest, 114(4):569-581. (Aug. 2004).
Jackson et al. (2006). "Widespread siRNA "off-target" transcriptsilencing mediated by seed region sequence complementarity." RNA 12(7): 1179-25 1187.

(Continued)

Primary Examiner — Amy H Bowman
(74) Attorney, Agent, or Firm — McDonnell Boehnen Hulbert & Berghoff LLP

(57) ABSTRACT

Disclosed herein are oligonucleotide sequences that generate innate immunity in cells within tumors upon its delivery into tumors. In certain embodiments, these oligonucleotides are specifically delivered into tumors through nanoparticles displaying targeting peptides that confer specific binding of the nanoparticle to receptors on the surface of tumor cells and allow for uptake of the nanoparticle into the tumor cells.

20 Claims, 8 Drawing Sheets
Specification includes a Sequence Listing.

(56) References Cited

OTHER PUBLICATIONS

"Janssens et al., ""Role of Toll-like receptors in pathogen recognition."" Clin Microbial Rev 16(4): 637-646. (2003)."

Judge et al., "Design of noninflammatory synthetic siRNA mediatingpotent gene silencing in vivo." Mol Ther 13(3): 494-505. (2006).

Judge et al.,"Sequence-dependent stimulation of the mammalianinnate immune response by synthetic siRNA." Nat Biotechnol 23(4): 457-462. (2005).

Kariko et al., "Exogenous siRNA mediates sequence-independentgene suppression by signaling through toll-like receptor 3." Cells Tissues Organs177(3): 132-138. (2004).

Kawai et al., "Innate immune recognition of viral infection." Nat Immunol7(2): 131-137. (2006).

Kim et al., "Interferon induction by siRNAs and ssRNAssynthesized by phage polymerase." Nat Biotechnol 22(3): 321-325. (2004).

Kim et al., "Strategies for silencing human disease using RNAinterference." Nat Rev Genet 8(3): 173-184.(2007).

Kleinman et al., "Sequence- and target-independentangiogenesis suppression by siRNA via TLR3." Nature 452(7187): 591-597. (2008).

Kumar et al., "Double-stranded RNA-dependent protein kinaseactivates transcription factor NF-kappa B by phosphorylating I kappa B." Proc NatlAcad Sci U S A 91(14): 6288-6292. (1994).

LaPlanche et al., Phosphorothioate-modified oligodeoxyribonucleatides. III. NMR and UV spectroscopic studies of the Rp-Rp, Sp-Sp, and Rp-Sp duplexes, [d(GGSAATTCC)]2, derived from diastereomeric O-ethyl phosphorothioates, Nucleic Acids Res, 14(22):9081-9083. (Nov. 1986).

Lau et al., "RNA-associated autoantigens activate B cells bycombined B cell antigen receptor/Toll-like receptor 7 engagement." J Exp Med202(9): 1171-1177. (2005).

Lee et al., "Molecular basis for the immunostimulatory activity ofguanine nucleoside analogs: activation of Toll-like receptor 7." Proc Natl Acad Sci US A 100(11): 6646-6651. (2003).

Lund et al., "Recognition of single-stranded RNA viruses byToll-like receptor 7." Proc Natl Acad Sci U S A 101(15): 5598-5603. (2004).

Manche et al., "Interactions between double-stranded RNAregulators and the protein kinase DAI." Mol Cell Biol 12(11): 5238-5248. (1992).

Matsumoto et al., "Toll-like receptor 3: a link between toll-likereceptor, interferon and viruses." Microbiol Immunol 48(3): 147-154. (2004).

Pisitkun et al., "Autoreactive B cell responses to RNA-relatedantigens due to TLR7 gene duplication." Science 312(5780): 1669-1672. (2006).

Poeck et al., "5'-Triphosphate-siRNA: turning gene silencing and Rig-I activation against melanoma." Nat Med 14(11): 1256-1263. (2008).

Robbins et al., "Misinterpreting the therapeutic effects of smallinterfering RNA caused by immune stimulation." Hum Gene Ther 19(10): 991-999. (2008).

Stein et al., "Physicochemical properties of phosphorothioate oligodeoxynucleotides", Nucleic Acids Res, 16(8):3209-3221. (Apr. 1988).

Subramanian et al., "A Tlr7 translocation accelerates systemicautoimmunity in murine lupus." Proc Natl Acad Sci U S A 103(26): 9970-9975. (2006).

Swann et al., "Immune surveillance of tumors." J Clin Invest117(5): 1137-1146. (2007).

Topalian et al., "Safety, activity, and immune correlates of anti-PD-1 antibody in cancer." N Engl J Med 366(26): 2443-2454. (2012).

Ulevitch, "Therapeutics targeting the innate immune system." Nat RevImmunol 4(7): 512-520. (2004).

Vollmer et al., ""Immune stimulation mediated by autoantigen bindingsites within small nuclear RNAs involves Toll-like receptors 7 and 8."" J Exp Med202(11): 1575-1585. (2005).

Whitmore et al., "Synergistic activation of innate immunity bydouble-stranded RNA and CpG DNA promotes enhanced antitumor activity." Cancer Res 64(16): 5850-5860. (2004).

Williams, "PKR; a sentinel kinase for cellular stress." Oncogene 18(45): 6112-6120. (1999).

Wolchok et al., "Nivolumab plus ipilimumab in advanced melanoma." N Engl J Med 369(2): 122-133. (2013).

Yoneyama et al., "The RNA helicase RIG-I has an essentialfunction in double-stranded RNA-induced innate antiviral responses." Nat Immunol5(7): 730-737. (2004).

International Search Report for International Application No. PCT/US2015/035879 dated Sep. 2, 2015. pp. 1-6.

Written Opinion for International Application No. PCT/US2015/035879 dated Sep. 2, 2015. pp. 1-10.

Bourquin et al.: "Immunostimulatory RNA oligonucleotides induce an effective antitumoral NK cell response through the TLR7", The Journal of Immunology, vol. 183, No. 10, Nov. 4, 2009, pp. 6078-6086.

Bourquin et al.: "Delivery of immunostimulatory RNA oligonucleotides by gelatin nanoparticles triggers an efficient antitumoral response", Journal of Immunotherapy, vol. 33, No. 9, Nov. 2010, pp. 935-944.

Friedberg et al.: "Combination immunotherapy with a CpG oligonucleotide (1018 ISS) and rituximab in patients with non-Hodgkin lymphoma: increased interferon-a/f3-inducible gene expression, without significant toxicity", Blood, vol. 105, No. 2, Jan. 15, 2005, pp. 489-495.

Friedberg et al.: "Phase II study of a TLR-9 agonist (1018 ISS) with rituximab in patients with relapsed or refractory follicular lymphoma", British Journal of Haematology, vol. 146, No. 3, Aug. 1, 2009, pp. 282-291.

Goodchild et al.: "Sequence determinants of innate immune activation by short interfering RNAs", BMC Immunology, vol. 10, No. 1, Jul. 24, 2009, p. 40.

Judge et al.: "Sequence-dependent stimulation of the mammalian innate immune response by synthetic siRNA", Nature Biotechnology, vol. 23, No. 4, Mar. 20, 2005, pp. 457-462.

Shirota et al.: "B cells capturing antigen conjugated with CpG oligodeoxynucleotides induce Th1 cells by elaborating IL-12", The Journal of Immunology, vol. 169, No. 2, 2002, pp. 787-794.

Sledz et al.: "Activation of the Interferon system by short-interfering RNAs", Nature Cell Biology, vol. 5, No. 9, 2003, pp. 834-839.

Yu et al.: "Lymphoid Neoplasia: Targeted nanoparticle delivery overcomes off-target immunostimulatory effects of oligonucleotides and improves therapeutic efficacy in chronic lymphocytic leukemia", Blood, Jan. 1, 2013, pp. 136-147.

\* cited by examiner

ANTI-TUMOR COMPOSITIONS AND METHODS

TECHNICAL FIELD

The invention generally concerns the fields of medicine and molecular biology. In particular, the invention relates to oligonucleotides that activate an anti-tumor innate immune response in a human or animal when targeted to a tumor, and methods for the use thereof.

BACKGROUND OF THE INVENTION

Some small interfering RNAs (siRNAs) can cause a variety of nonspecific side effects, including the stimulation of interferon and cytokine production, global shutdown of protein synthesis, nonspecific degradation of mRNAs, and off-target effects resulting in nonspecific reduction of expression of genes (Robbins et al., 2009). For many siRNA applications, specific gene silencing is preferred, and activation of innate immunity in a subject following administration of siRNA is considered an undesirable side effect.

In cancer therapy, however, these immunostimulatory siRNAs, or "isRNAs", can be used as potent immunomodulatory agents, for activating beneficial effects including proliferation blockage, differentiation, and apoptosis that are desirable in cancer cells. Thus, the innate immune system can serve as an tumor suppressor (Shankaran et al., 2001; Bui and Schreiber, 2007; Koebel et al., 2007), and immunostimulating agents can be used in antitumor therapy.

However, there remains a need for effective techniques that are capable of restricting isRNA activation of the innate immune response to tumor cells and not generally in non-tumor cells in a human or animal.

SUMMARY OF THE INVENTION

Applicants disclose herein compositions and methods for delivering isRNA complexes specifically to tumor cells in a human or animal. Once these complexes are delivered to tumor cells, the isRNA complexes can activate the innate immune response of a subject specifically in tumor cells, thus inducing beneficial effects including but not limited to proliferation blockage, differentiation, and apoptosis, among others.

In one aspect, disclosed herein is a composition for targeting and inhibiting tumor cell growth. In certain embodiments the composition comprises an isolated oligonucleotide capable of activating an innate immune response within tumors; a tumor cell-targeting moiety; and a pharmaceutically acceptable salt thereof.

In one aspect, disclosed herein is a composition for targeting and inhibiting tumor cell growth comprising an isolated oligonucleotide capable of activating an innate immune response within tumors. In one embodiment, the oligonucleotide of the composition comprises the nucleic acid sequence of SEQ ID NO: 1. In another embodiment, the oligonucleotide comprises the nucleic acid sequence of SEQ ID NO: 2. In certain embodiments, the oligonucleotide is double stranded. In one embodiment, the oligonucleotide is double stranded, and a strand comprises the nucleic sequence of SEQ ID NO: 1 and a strand comprises the nucleic sequence of SEQ ID NO: 2. In another embodiment, the oligonucleotide is double stranded, and a strand comprises the nucleic sequence of SEQ ID NO: 3 and a strand comprises the nucleic sequence of SEQ ID NO: 4. In yet another embodiment, the oligonucleotide is double stranded, and a strand comprises the nucleic sequence of SEQ ID NO: 5 and a strand comprises the nucleic sequence of SEQ ID NO: 6. In certain embodiments, the oligonucleotide of the composition comprises one or more UG motifs. In some embodiments, the nucleic acid sequence of the oligonucleotide of the composition comprises one or more UG motifs or is UG-rich.

In other embodiments, the oligonucleotide of the disclosed composition for targeting and inhibiting tumor cell growth comprises at least one modified nucleotide that promotes the activation of the innate immune system in a cell. In one embodiment, the modified nucleotide comprises a modified ribose. In another embodiment, the modified nucleotide comprises an O-methyl or fluoro modification. In certain embodiments, the modified nucleotide is located at the second position from the 5' end of the oligonucleotide of the disclosed composition.

In another aspect, disclosed herein is a composition for targeting and inhibiting tumor cell growth comprising a tumor cell-targeting moiety. In certain embodiments, the tumor cell-targeting moiety is a protein, a peptide, or an aptamer. In certain embodiments, the tumor cell-targeting moiety comprises any of the cell-targeting moieties or domains as disclosed in of U.S. Pat. No. 8,680,045, hereby incorporated by reference in its entirety for any purpose.

In another aspect, the composition for targeting and inhibiting tumor cell growth as disclosed herein further comprises a nanoparticle. In some embodiments, the nanoparticle comprises lipids, cyclodextrin, chitosan, carbohydrate polymers, elastin-like polymers (ELP), calcium phosphate polymers, or combinations thereof. In one embodiment, the nanoparticle is PEGylated. In one specific embodiment, the nanoparticle is ELP-L.

In another embodiment, the composition for targeting and inhibiting tumor cell growth as disclosed herein is encapsulated in a liposome. In one embodiment, the liposome is PEGylated.

In another aspect, disclosed herein is a pharmaceutical composition comprising the disclosed composition for targeting and inhibiting tumor cell growth. In certain embodiments the pharmaceutical composition comprises the compositions disclosed herein and a pharmaceutically acceptable carrier, excipient or adjuvant. In other embodiments, the pharmaceutical composition comprises the compositions disclosed herein and a chemotherapeutic drug or agent. In yet other embodiments, the pharmaceutical composition comprises the compositions disclosed herein and an immunity checkpoint inhibitor.

In another aspect, disclosed herein is a method for inhibiting growth of a tumor cell. In certain embodiments, the method comprises providing a composition comprising an oligonucleotide that is capable of activating the innate immune response in the tumor cell, and contacting the tumor cell with the composition in an amount sufficient to inhibit tumor cell growth. In some embodiments, the composition is the composition for targeting and inhibiting tumor cell growth as disclosed herein.

In another aspect, disclosed herein is a method for activating a subject's innate immune response specifically in the tumor cells of the subject. In some embodiments, the method comprises obtaining an oligonucleotide that is capable of activating the innate immune response in a tumor cell; contacting the oligonucleotide with a tumor cell-targeting moiety to form a composition, such that the composition will specifically deliver the oligonucleotide to tumor cells in the subject; and administering a pharmaceutically effective amount of the composition to the subject.

In certain embodiments, the tumor cell of any of the disclosed methods is a human bladder cell, a human breast cell, a human colon cell, a human liver cell, a human lung cell, a human neuroblastoma cell, a human ovarian cell, a human pancreatic cell, a human prostate cell, or a human skin cell.

DETAILED DESCRIPTION

Figure 1:
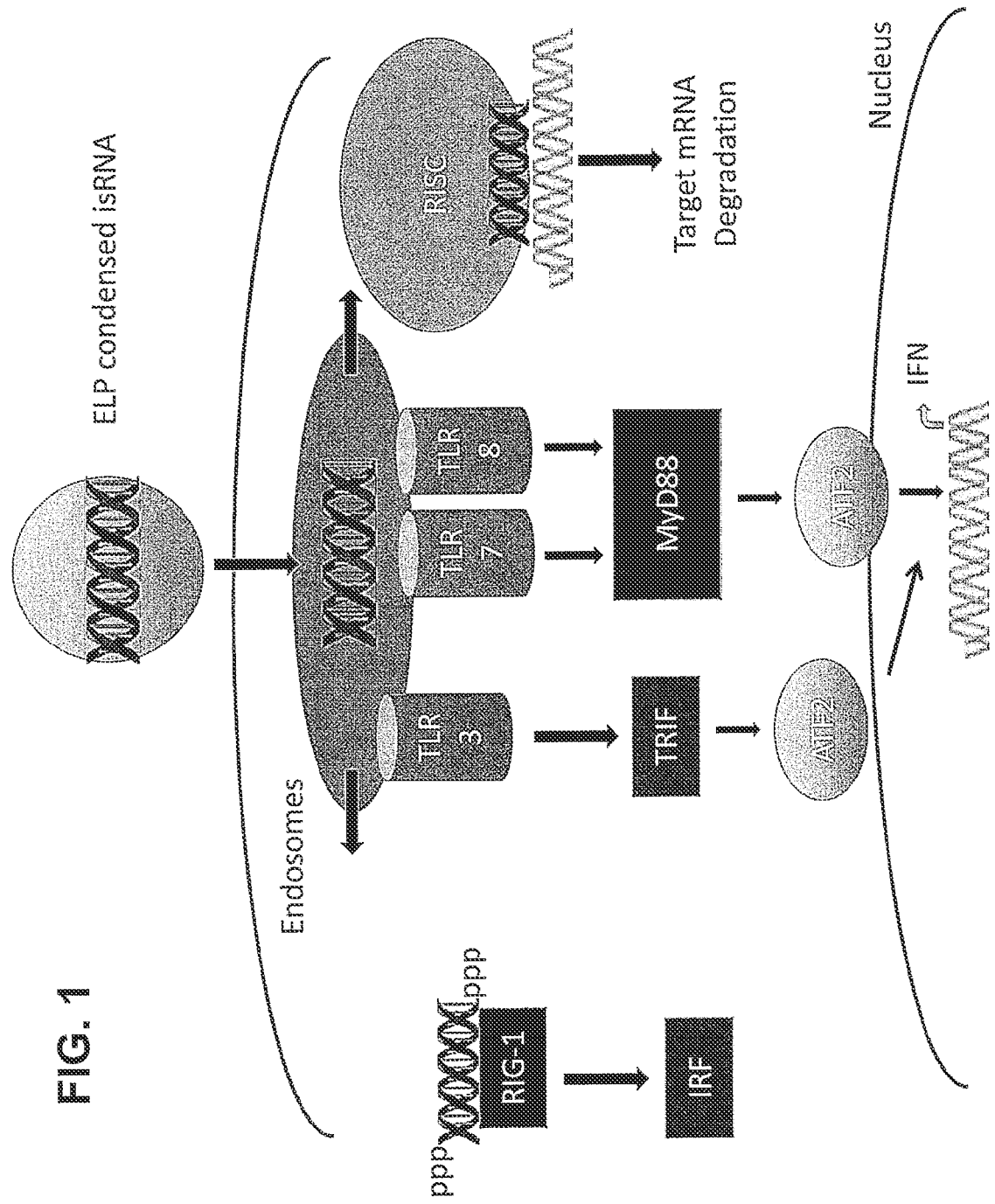
FIG. 1 depicts siRNA interactions with toll-like receptors (TLRs) and the RNA interference gene silencing pathway. Various TLRs are depicted. TLR7 and TLR8 recognize single-stranded RNA (ssRNA) motifs, but may also recognize certain motifs in double-stranded RNA (dsRNA). TLR3 binds dsRNA and signals through a different pathway from TLR7 and TLR8. RIG-1 recognizes triphosphate-containing RNAs. siRNAs that escape the endosome can enter the RNAi pathway where one of the two strands is selected as a guide strand and directs sequence-specific message degradation of a complementary RNA.

In one aspect, disclosed herein are oligonucleotides that are capable of activating the innate immune response in tumor cells. As used herein, the term "innate immune response" refers to non-antigen-specific responses in cells and tissues in a human or animal, preferably differentially or preferentially induced in tumor cells. It also refers to cellular changes that affect the abilities of cells to act as antigen-presenting cells and/or modulate the antigen-specific adaptive immune response. In one embodiment, the innate immune response comprises activation of natural killer (NK) cell activity. NK cells are involved in the first line of defense against pathogens. In another embodiment, the innate immune response comprises production and/or secretion of one or more cytokines or growth factors such as in non-limiting examples IFN-α, IFN-γ, IL-1, IL-6, IL-10, IL-12, and TNF-α. Innate immunity may further comprise involvement of macrophages, dendritic cells and monocytes.

The immune system is capable of identification and elimination of tumor cells on the basis of their expression of tumor-specific antigens or molecules induced by cellular stresses. Tumor cells can escape from tumor immune surveillance, however, and therapies targeted to enhance anti-tumor immunity are currently in development (Swann and Smyth 2007).

The isRNA oligonucleotides described herein are, in certain embodiments, duplexes of chemically-synthesized oligoribonucleotides. These isRNA duplexes have beneficial effects on the immune system. While not intending to be bound by any particular theory or mechanism, the oligonucleotides disclosed herein are believed to activate the innate immune response by activating Toll-like Receptors (TLRs) on and within tumor cells. Once activated, cytokines and other cytotoxic enzymes are released from dendritic cells, monocyte/macrophages, and natural killer cells. Normally, this effect is viewed as an adverse event in clinical practice particularly involving administration of conventional siRNA molecules as inter alia therapeutic agents.

The mammalian innate immune system recognizes a number of nucleic acid species as signatures of potential pathogens. Specific TLRs have been identified that recognize double-stranded RNA (TLR3) (Alexopoulou, Holt et al. 2001) and single-stranded RNA (ssRNA) (TLR7 and TLR8) (Diebold, Kaisho et al. 2004; Heil, Hemmi et al. 2004; Lund, Alexopoulou et al. 2004) in both humans and mice. These nucleic acid—sensing TLRs are localized intracellularly and induce Type I interferons such as IFN-α and inflammatory cytokines upon activation. TLR7 is typically expressed by plasmacytoid dendritic cells and B cells and is activated by ssRNA viruses and synthetic ssRNA rich in guanosine and uridine. TLR7 and TLR8 are typically expressed on distinct immune cell types, yet these TLRs recognize similar nucleic acids. Murine TLR8 does not respond to conventional TLR7/8 ligands and, until recently was thought to be non-functional in mice (Diebold, Kaisho et al. 2004). RNA can also generate interferon responses through TLR- and dsRNA-dependent protein kinase (PKR)-independent mechanisms, including the cytoplasmic RNA receptors RIG-1 and Mda-5 (Yoneyama, Kikuchi et al. 2004).

When a ligand binds to a TLR, a signal is transmitted to the nucleus and genes encoding synthesis of intracellular regulatory molecules are expressed (Ulevitch 2004). Activation of the immune system through TLRs causes rapid production of proinflammatory cytokines and interferons that orchestrate the developing innate and adaptive immune responses to infection. Aberrant or excessive stimulation of these pathways is thought to underlie many inflammatory and autoimmune disorders. For example, RNA- and DNA-associated autoantigens in systemic lupus erythematosus have been shown to drive pathologic autoantibody and interferon production through TLR7 and TLR9 activation (Lau, Broughton et al. 2005; Vollmer, Tluk et al. 2005; Christensen, Shupe et al. 2006; Pisitkun, Deane et al. 2006; Subramanian, Tus et al. 2006).

TLR3 is a known receptor for double-stranded RNA. TLR3 is expressed on dendritic cells, fibroblasts, macrophages, and epithelial cells (Matsumoto, Funami et al. 2004). The adaptor molecule for TLR3 is TICAM-I, wherein binding of TLR3 to TICAM-I induces multiple signaling cascades that ultimately lead to production of type I interferons (IFN-αβ) (Matsumoto, Funami et al. 2004). The interferons are cytokines that induce uninfected cells to produce enzymes capable of degrading RNA, thus preventing viral replication. Interferons also activate a variety of cells important to defense including cytoxic T-lymphocytes, macrophages, and NK cells.

Single-stranded RNA recognition is mediated in mice by Toll-like receptor 7 and in humans by TLR-8. In mice, TLR7 binds to the adaptor MyD88 and leads to activation of IFN-α. Diebold et al. (Diebold, Kaisho et al. 2004) showed that influenza virus RNA, polyuridylic acid, and in vitro-synthesized mRNA all induced IFN-α production in plasmacytoid dendritic cells. Heil et al. (Heil, Hemmi et al. 2004) showed that guanine- and uridine-rich RNA oligonucleotides of 20 residues with phosphorothioate termini stimulated dendritic cells and macrophages to secrete INF-α and proinflammatory and regulatory cytokines. Using TLR-deficient mice, these authors also showed that mouse TLR-7 and human TLR-8 were responsible for binding to single-stranded RNA. Human TLR-7 is also activated by guanine nucleotide analogs (Lee, Chuang et al. 2003).

Double-stranded RNA can also activate the innate immune system through interaction with a ubiquitously-expressed serine/threonine protein kinase called PKR. PKR is part of the TLR4 cascade activated by TLR4 binding of bacterial LPS. PKR is induced by interferon and activated by dsRNA, cytokines, growth factors, and stress signals. PKR is autophosphorylated and activated upon binding to dsRNA. Activation results in inhibition of protein synthesis via eIF2a phosphorylation and also induces transcription of inflammatory genes by PKR-dependent signaling of the activation of different transcription factors (Williams 1999). PKR up-regulates NF-κB expression through phosphorylation of its inhibitor IkB (Kumar, Haque et al. 1994). As few as 11 base pairs of dsRNA can bind to PKR and induce activity, but maximal activation requires at least 30 base pairs (Manche, Green et al. 1992).

The isRNA agents described herein may activate the innate immune system through one of the receptors known to bind nucleic acids or nucleotide analogs. There have been reports that siRNA duplexes are able to trigger an immune response in human cells under certain conditions. Sledz et al. (Sledz and Williams 2003) reported induction of the interferon system with each of the six different siRNA duplexes tested. Bridge et al. (Bridge, Pebernard et al. 2003) reported that some shRNAs delivered using viral vectors induced expression of an interferon-stimulated gene. These two reports showed that the siRNA duplexes activated PKR. In contrast, data from Kariko et al. implicated the TLR3 pathway and TLR3 activation was concentration dependent (Kariko, Bhuyan et al. 2004).

Activation of the innate immune response is advantageous in diseases ranging from viral infections to cancer (Whitmore, DeVeer et al. 2004). isRNA agents should activate innate immunity, which, in turn should shape the adaptive immune response. Some isRNA sequences and modifications may better activate the innate immune response than others. This activation could come via any of the Toll-like receptor pathways that are known to bind nucleic acids: TLR3, a receptor for double-stranded RNA; TLR8, a receptor for single-stranded RNA; or PKR, a protein kinase activated by dsRNA. Each of these proteins is known to bind to molecules similar to the isRNA agents described.

Further disclosed herein are isRNA oligonucleotide agents that are either unmodified or modified so as to have an effect, or to specifically avoid having an effect, on the immune system of a subject. While not wishing to be bound by theory, it is believed that modulation of immune system activity can result from an interaction of the isRNA agent with a component of the immune system, where the interaction disrupts or stimulates an activity of the component. These effects are independent of RISC-mediated gene silencing, as in traditional uses of siRNA molecules for RNAi applications. In contrast, the isRNA molecules disclosed herein are believed to act through an interaction of single-stranded or double-stranded RNA with a protein component of the immune system.

In another aspect of the disclosure, the oligonucleotides capable of activating the innate immune response within tumors comprise specific nucleotide sequences. Oligonucleotide sequences used to demonstrate the effect of specific delivery of isRNA duplexes to tumor cells are shown below in Table 1, wherein "m" appearing in the sequences of Table 1 denotes a modification of the 2' ribose position of the indicated nucleoside base and dT indicates deoxyribothymidine.

TABLE 1 isRNA oligonucleotide sequences

| SEQ ID NO. | Oligonucleotide Sequence |
| --- | --- |
| 1 | 5'-AAUUCUCCGAACGUGUCAC-3 |
| 2 | 5'-GUGACACGUUCGGAGAAUU-3' |
| 3 | 5'-AmAUUCUCCGAACGUGUCACdTdT-3 |
| 4 | 5'-GmUGACACGUUCGGAGAAUUdTdT-3' |
| 5 | 5'-AmAmUmUCmUCCmGAACmGmUmGmUCACdTdT-3' |
| 6 | 5'-mGmUmGACACmGmUmUCmGmGAmGAAmUmUdTdT-3' |

In certain embodiments, oligonucleotides disclosed herein are annealed to form a double-stranded duplex of isRNA. In one embodiment, the double stranded oligonucleotides disclosed herein comprise a strand comprising the nucleic sequence of SEQ ID NO: 1 and a strand comprising the nucleic sequence of SEQ ID NO: 2. In another embodiment, the double stranded oligonucleotides disclosed herein comprise a strand comprising the nucleic sequence of SEQ ID NO: 3 and a strand comprising the nucleic sequence of SEQ ID NO: 4. In yet another embodiment, the double stranded oligonucleotides disclosed herein comprise a strand comprising the nucleic sequence of SEQ ID NO: 5 and a strand comprising the nucleic sequence of SEQ ID NO: 6.

The isolated oligonucleotides and isRNA duplexes disclosed herein can be produced by conventional molecular biology techniques. For example, production of the subject dsRNAs (e.g., siRNAs) can be carried out by chemical synthetic methods or by recombinant nucleic acid techniques. The term "dsRNA" as used herein refers to a double stranded RNA molecule capable of RNA interference (RNAi), including siRNA. Methods of forming double-stranded RNA duplexes and other isRNA preparation techniques are disclosed in Judge 2006, which is hereby incorporated by reference in its entirety. Endogenous RNA polymerase of the treated cell can mediate transcription in vivo, or cloned RNA polymerase can be used for transcription in vitro.

As used herein, dsRNA or siRNA molecules of the application need not be limited to those molecules containing only RNA, but can further encompass chemically modified nucleotides and non-nucleotides. For example, dsRNAs disclosed herein can include modifications to either the phosphate-sugar backbone or the nucleoside, e.g., to reduce susceptibility to cellular nucleases, improve bioavailability, improve formulation characteristics, and/or change other pharmacokinetic properties. To illustrate, the phosphodiester linkages of natural RNA can be modified to include at least one of a nitrogen or sulfur heteroatom. Modifications in RNA structure can be tailored to allow specific genetic inhibition while avoiding a general response to dsRNA. Likewise, bases can be modified to block, inter alia, adenosine deaminase activity. The dsRNAs can be produced enzymatically or by partial or total organic synthesis, wherein any modified ribonucleotide can be introduced by in vitro enzymatic or organic synthesis. Methods of chemically modifying RNA molecules can be adapted for modifying dsRNAs. Merely to illustrate, the backbone of an dsRNA or siRNA can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration). In certain cases, the dsRNAs of the application lack 2'-hydroxy(2'-OH) containing nucleotides. In certain embodiments, the siRNA molecules comprise a phosphorothioate sense strand. In certain embodiments, the siRNA molecules comprise a phosphodiester antisense strand. One exemplary method of generating modified RNA molecules is disclosed in Robbins, 2008, which is incorporated by reference in its entirety.

Unless specified otherwise, sequences depicted herein follow the convention therein the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "polynucleotide" as used herein means a polymeric form of nucleotides that are at least 10 bases in length. In certain embodiments, the bases can be ribonucleotides or deoxyribonucleotides or a modified form of either type of nucleotide. The term includes single and double stranded forms of DNA or RNA.

The term "oligonucleotide" as used herein includes naturally occurring, and modified nucleotides linked together by naturally occurring, and/or non-naturally occurring oligonucleotide linkages. Oligonucleotides are a polynucleotide subset generally comprising no more than 200 nucleotides. In certain embodiments, oligonucleotides are 10 to 60 nucleotides in length. In certain embodiments, oligonucleotides are 12, 13, 14, 15, 16, 17, 18, 19, 20, 21, or 30 to 40 bases in length.

Oligonucleotides can be single stranded, e.g. for use as antisense RNAs, or double-stranded, as small interfering RNAs (siRNAs) or small (or short) hairpin RNAs (shRNAs).

An oligonucleotide can include a detectable label, such as a radiolabel, a fluorescent label, an antigenic label or a hapten.

The term "obtaining" means taking physical possession of the physiological specimen. The manner in which the material is acquired is not limited to any specific process.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphate, phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, Nucl. Acids Res. 14: 9081; Stec et al., 1984, J. Am. Chem. Soc. 106: 6077; Stein et al., 1988, Nucl. Acids Res. 16: 3209; Zon et al., 1991, Anti-Cancer Drug Design 6: 539; Zon et al., 1991, Oligonucleotides and Analogues: A Practical Approach, (F. Eckstein, ed.), Oxford University Press, Oxford England, pp. 87-108; Stec et al., U.S. Pat. No. 5,151,510; Uhlmann and Peyman, 1990, Chemical Reviews 90: 543, the disclosures of each of which are hereby incorporated by reference for any purpose.

As used herein, the term "isolated polynucleotide" or "isolated oligonucleotide" means a polynucleotide of genomic, cDNA, or synthetic origin or a combination thereof, which by virtue of its source the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

The term "transfection" is used to refer to the uptake of foreign or exogenous nucleotides by a cell, and a cell has been "transfected" when the exogenous nucleotides have been introduced inside the cell. A number of transfection techniques are well known in the art and are disclosed herein. See, e.g., Graham et al., 1973, Virology 52: 456; Sambrook et al., 2001, Molecular Cloning: A Laboratory Manual, 3d ed., Cold Spring Harbor Laboratory Press, Cold Spring Harbor, N.Y.; Davis et al., 1986, Basic Methods in Molecular Biology (Elsevier); and Chu et al., 1981, Gene 13: 197.

In certain embodiments, the oligonucleotides disclosed herein can comprise a delivery vehicle, including liposomes and nanoparticles, for administration to a subject; carriers and diluents and their salts; and can be present in pharmaceutical compositions. In a particular embodiment, isRNA is delivered in association with an ELP-L nanoparticle, as disclosed in U.S. Pat. No. 8,680,045, which is hereby incorporated by reference in its entirety. Methods for the delivery of nucleic acid molecules are described, for example, in Akhtar et al., 1992, Trends Cell Bio. 2:139; Delivery Strategies for Antisense Oligonucleotide Therapeutics, ed. Akhtar, 1995, Maurer et al., 1999, Mol. Membr. Biol. 16:129-140; Hofland and Huang, 1999, Handb. Exp. Pharmacol., 137:165-192; and Lee et al., 2000, ACS Symp. Ser. 752:184-192, all of which are incorporated herein by reference. Beigelman et al., U.S. Pat. No. 6,395,713 and Sullivan et al., PCT WO 94/02595, further describe general methods for delivery of nucleic acid molecules into cells and tissues. These protocols can be utilized for the delivery of virtually any nucleic acid molecule into a cell. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722).

The nanoparticles disclosed herein are typically chemically based shell structures that bind up a nucleotide or drug agent and stabilize the molecule in the blood. Nanoparticles often comprise sugar, dextran, calcium phosphate, chitosan, peptide and/or plastic polymers. Drug agent-loaded nanoparticles for cancer drug delivery preferably have the following properties: 1) be easy to synthesize in a few steps with high yield and purity; 2) assemble into monodisperse drug-loaded nanoparticles with a size below 100 nm; 3) allow encapsulation of diverse drugs; 4) exhibit favorable pharmacokinetics and tumor accumulation; 5) release the drug with controlled and tunable kinetics; 6) lead to a therapeutic response; and 7) degrade into non-toxic components to enable clearance from the body without adverse toxicity. Although a number of different nanoscale delivery systems have been proposed for cancer therapy, most do not satisfy these criteria, which are critical to move these systems into clinical practice.

It is believed that the ELP drug delivery nanoparticle specifically enters tumors due to the enhanced permeability and retention (EPR) effect, which results from abnormalities of tumor blood and lymphatic vasculature. By using ELP nanoparticles disclosed herein, the innate immune system is only activated within tumors, and the systemic activation of the innate immune system is prevented. However, the invention is not limited to ELP-nanoparticles. Other embodiments of the inventions can utilize liposomes, polydextran, or other polymers that (1) can carry a nucleotide molecule, (2) can or cannot carry a conventional chemotherapeutic agent, and (3) can accommodate a peptide molecule that targets specific tumor types.

Alternatively, the nucleic acid/vehicle combination can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., 1999, Clin. Cancer Res. 5:2330-2337 and Barry et al., International PCT Publication No. WO 99/31262. Many examples in the art describe delivery methods of oligonucleotides by osmotic pump (see Chun et al., 1998, Neuroscience Letters 257:135-138, D'Aldin et al., 1998, Mol. Brain Research 55:151-164, Dryden et al., 1998, J. Endocrinol. 157:169-175, Ghirnikar et al., 1998, Neuroscience Letters 247:21-24) or direct infusion (Broaddus et al., 1997, Neurosurg. Focus 3, article 4). Other delivery routes include, but are not limited to oral delivery (such as in tablet or pill form) and/or intrathecal delivery (Gold, 1997, Neuroscience 76:1153-1158). More detailed descriptions of nucleic acid delivery and administration are provided in Sullivan et al., PCT WO 94/02595, Draper et al., PCT WO93/23569, Beigelman et al., PCT WO99/05094, and Klimuk et al., PCT WO99/04819, all of which are incorporated by reference herein.

In certain embodiments, the compositions disclosed herein comprise an oligonucleotide and a cell-targeting moiety (also referred to as cell targeting domain, or CTD). In certain embodiments, the cell targeting moiety is a polypeptide. Exemplary cell targeting polypeptides are disclosed in U.S. Pat. No. 8,680,045, which is herein incorporated by reference in its entirety.

The CTD is not limited to any particular polypeptide sequence. It can be designed to target any desired biological molecule. In particular embodiments, the biological molecule is specifically expressed in a desired cell type. Any cell can be selected for targeting. In certain embodiments, the target cell is a eukaryotic cell, more preferably a mammalian cell and most preferably a rodent or human cell. In particular embodiments, the target cell is a tumor cell. Non-limiting examples of a tumor cell contemplated by the current invention include tumor cell is a human bladder cell, a human breast cell, a human colon cell, a human liver cell, a human lung cell, a human neuroblastoma cell, a human ovarian cell, a human pancreatic cell, a human prostate cell, or a human skin cell. In addition, a target cell can be selected based on the disease or condition that affects a patient who is to be treated by methods of the invention.

In one aspect, CTDs were designed as disclosed herein to target biological molecules that are expressed in tumor cells but are not expressed in non-tumor cells (e.g. a tumor cell-targeting moiety). The oligonucleotides disclosed herein are designed to be specifically delivered into tumors using nanoparticles displaying a cell targeting moiety. In certain embodiments, the CTD of the polypeptide comprises peptide ligands specific for tumor cells. These cell-targeting moieties can confer specific binding of the nanoparticle to receptors on the surface of tumor cells and allow for uptake of the nanoparticle specifically into the tumor cells by endocytosis, pinocytosis, or other cell membrane-involved mechanism. In one embodiment, the CTD comprises a peptide ligand that binds the L1 cell adhesion molecule (L1 CAM). Targeting specific tumor cells is advantageous due to the reduction of side-effects of cancer therapy by specific targeting of the drugs delivered in tumor-seeking ELP nanoparticles. As disclosed herein, the use of CTD with isRNA molecules can reduce activation of the innate immune response in non-tumor cells, thus reducing undesirable side effects in subjects administered with isRNA.

In other embodiments, the nanoparticle can condense such that the nanoparticle is permeable to the cell membrane. In such alternative embodiments, the nanoparticle can contact the biological molecules inside of the cell, such as TLRs in endosomes and other innate immunity activators in the cytoplasm.

In a further embodiment of the invention, additional targeting ligands are associated with the liposome or nanoparticle containing the drug agent, that target receptors on tumor cells designated for apoptotic destruction. Liposomes can also be coated with polyethylene glycol (i.e., are PEGylated) to prolong the lifetime of the liposomes in the circulation. Similarly, nanoparticles can be so coated.

Targeting molecules can be organic chemical linkers termed aptamers that specifically bind receptors on the surface of a target cell. The aptamers can be covalently linked to the lipids of the liposome or polymers of the nanoparticles. Other molecules that can be used to target liposomes or nanoparticles to tumor cells are peptides, proteins or antibodies that are directed to a specific receptor on the surface of tumor cells.

In certain embodiments, disclosed herein are pharmaceutical compositions comprising a therapeutically effective amount of an oligonucleotide, nanoparticle, and/or drug agent as provided herein together with a pharmaceutically acceptable diluent, carrier, solubilizer, emulsifier, preservative and/or adjuvant. The term "pharmaceutical composition" as used herein refers to a composition comprising a pharmaceutically acceptable carrier, excipient, or diluent and a chemical compound, peptide, or composition as described herein that is capable of inducing a desired therapeutic effect when properly administered to a patient. The term "therapeutically effective amount" refers to the amount of a pharmaceutical composition of the invention or a compound identified in a screening method of the invention determined to produce a therapeutic response in a mammal. Such therapeutically effective amounts are readily ascertained by one of ordinary skill in the art and using methods as described herein.

The invention further provides pharmaceutical compositions comprising an oligonucleotide, polypeptide, nanoparticle, or drug agent as provided herein. In particular, isRNA oligonucleotides and other drug agents are delivered in association with an ELP nanoparticle, for example the ELP-L nanoparticle.

Acceptable formulation materials preferably are nontoxic to recipients at the dosages and concentrations employed. The pharmaceutical composition can contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (Such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, polyethylene glycol (PEG), sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, Remington's Pharmaceutical Sciences, 18th Edition, (A. R. Gennaro, ed.), 1990, Mack Publishing Company.

In another aspect, the isRNA oligonucleotides disclosed herein may also be used in conjunction with a second therapeutic, which may be a chemotherapeutic agent, an antibiotic, or a second RNA agent. In certain embodiments, the isRNA oligonucleotides disclosed herein are used in pharmaceutical compositions in combination with immune checkpoint inhibitors. This combination of drugs is capable of removing the blockade in tumor cells of immune responses as conferred by immune checkpoint inhibitors, while the isRNAs disclosed herein activate the innate immune system. As such, a synergistic effect on immune response activation may be observed using this combination of agents. Exemplary immune checkpoint targets are listed in Table 2.

TABLE 2

Immune Checkpoint Targets.

| Symbol | Gene Target | Accession Number |
|---|---|---|
| PDL1 | Programmed cell death protein 1 ligand | AY254342.1 |
| CD80 | Cluster of Differentiation 80 | NM_005191.3 |
| CD86 | Cluster of Differentiation 86 | NM_001206924.1 |
| CD276 | Cluster of Differentiation 276 | NM_001024736.1 |
| VTCN1 | V-set domain containing T cell activation inhibitor 1 | NM_001253850.1 |
| ICOS | Inducible T cell co-stimulator | NM_012092.3 |
| CTLA4 | cytotoxic T-lymphocyte-associated antigen 4 | AF414120.1 |
| HVEM | herpesvirus entry mediator | NM_003820.3 |
| BTLA | B and T lymphocyte attenuator | NM_181780.3 |
| KIR | killer cell immunoglobulin-like receptor | NM_013289.2 |
| LAG3 | lymphocyte activation gene 3 | NM_002286.5 |
| GAL9 | Galectin 9 | NM_001042685.1 |
| TIM3 | T cell membrane protein 3. | NM_032782.4 |

Immune checkpoint inhibitors can be, for example, therapeutic antibodies, inhibitory nucleotides, or small molecule inhibitors. For example, many antibodies that act as immune checkpoint inhibitors are known in the art, such as pembrolizumab (MK-3475, Merck), nivolumab (BMS-936558, Bristol-Myers Squibb), pidilizumab (CT-011, CureTech Ltd.), AMP-224 (Merck), MDX-1105 (Medarex), MED14736 (MedImmune), MPDL3280A (Genentech), BMS-936559 (Bristol-Myers Squibb), ipilimumab (Bristol-Myers Squibb) and tremelimumab (Pfizer). Other compounds that suppress the immune system may also be useful in treating cancer, including disruption of the PKR pathway. (Pikarsky et al., Nature, 2004, 431, 461-466; Huber et al., J. Clin. Invest., 2004, 114, 569-581).

Additional pharmaceutical compositions are evident to those skilled in the art, including formulations involving nanoparticles or compounds of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations can include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, Biopolymers 22: 547-556), poly(2-hydroxyethyl-methacrylate) (Langer et al., 1981, J. Biomed. Mater. Res. 15: 167-277) and Langer, 1982, Chem. Tech. 12: 98-105), ethylene vinyl acetate (Langer et al., id.) or poly-D(-)-3-hydroxybutyric acid (EP 133.988). Sustained release compositions can also include liposomes, which can be prepared by any of several methods known in the art. See e.g., Eppstein et al., 1985, Proc. Natl. Acad. Sci. USA 82: 3688-3692; EP 036,676; EP 088,046 and EP 143,949.

EXAMPLES

The invention is further illustrated by the following examples which should not be construed as further limiting. The contents of Sequence Listing, Figures and all references, patents and published patent applications cited throughout this application are expressly incorporated herein by reference.

Furthermore, in accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization [B. D. Hames & S. J. Higgins eds. (1985)]; Transcription And Translation [B. D. Hames & S. J. Higgins, eds. (1984)]; Animal Cell Culture [R. I. Freshney, ed. (1986)]; Immobilized Cells And Enzymes [IRL Press, (1986)]; B. Perbal, A Practical Guide To Molecular Cloning (1984); F. M. Ausubel et al. (eds.), Current Protocols in Molecular Biology, John Wiley & Sons, Inc. (1994).

Example 1: Evaluation of isRNA Delivery and Uptake to Peripheral Blood Mononuclear Cells (PBMCs)

Peripheral blood mononuclear cells (PBMCs) from whole blood were purchased (Allcells, Alameda, Calif.) and cultured in 6 well plates. Generally, PBMCs are comprised of lymphocytes (including T-cells, B-cells, NK cells, etc.) and monocytes.

To evaluate the uptake of isRNA into PBMCs, fluorescently-labeled nontargeted siGLO control siRNA (Dharmacon), was condensed with either DharmaFect 4 (DF4) (Dharmacon), a commercial liposome formulation, or with ELP-L, a polypeptide-based nanoparticle, which is described in U.S. Pat. No. 8,680,045, which is incorporated by reference in its entirety for any purpose.

isRNA:ELP-L nanocomplexes were confirmed by incubating 100 pmol (1.33 µg) isRNA with increasing concentrations of ELP-L protein for 30 min at room temperature. The products were then subjected to electrophoretic separation on a 1% agarose gel in 1×TAE buffer at 120 V for 30 min. Specific binding of isRNA into the ELP-L nanoparticle increases its size approx. 500-fold from 35,000 Daltons. Hence, the isRNA/ELP-L nanocomplex formation was confirmed by the observed retention of nanocomplex within the wells of the agarose gel due to its high molecular weight (data not shown). Nanocomplexes of isRNA/ELP-L were formulated in this manner for the all in vitro and in vivo studies.

Figure 2:
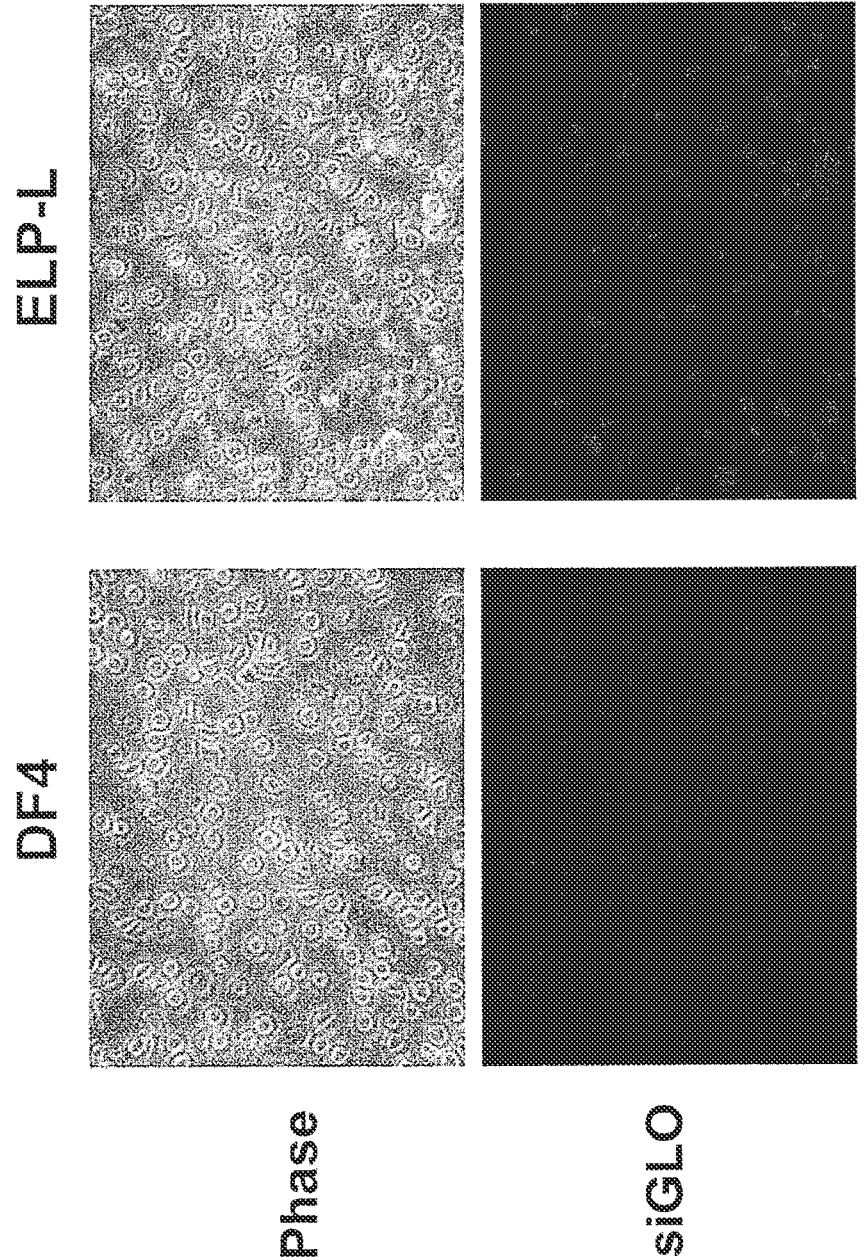
FIG. 2 depicts uptake of siGLO into peripheral blood mononuclear cells (PBMCs) when complexed with either DF4 or ELP-L. PBMC were transfected with siGLO control at 50 nM using DharmaFECT (DF4) or ELP-L nanoparticles for 16 h.

Uptake of the condensed siGLO siRNA into PBMCs was quantified by flow cytometry and observed using an Olympus IMT-2 fluorescence microscope at 40× magnification. As shown in FIG. 2, there was a far greater uptake of siGLO in cells exposed to ELP-L nanocomplexes than those of DF4.

Example 2: Effect of isRNA on Human Ovarian Cancer Cells Activated by PBMCs

A SKOV-3 cell line (human ovarian cancer cells) that stably expresses firefly luciferase was generated from the pGL-3 plasmid (Promega) using conventional molecular biology techniques. Luciferase expression from this cell line (referred to as SKOV-3 GL3) was used as a surrogate for cell viability in the following studies.

The isRNA duplex was generated by Dharmacon (Lafayette, Colo.). In brief, oligonucleotides according to SEQ ID NO: 1 and SEQ ID NO: 2 were synthesized and converted to the 2'-hydroxyl form, annealed, desalted, dialyzed, and sterile-filtered, thus generating the isRNA duplex. Additional details regarding the formation of double-stranded RNA duplexes and other isRNA preparation techniques are disclosed in Judge 2006, which is hereby incorporated by reference in its entirety. The identity of the duplex was confirmed using MALDI-TOF mass spectrometry. The isRNA duplex was then condensed with either DF4 or ELP-L, as described above, along with siGLO as a control siRNA molecule.

PBMC were treated with the isRNA or siGLO complexed with either DF4 or ELP-L at 50 nM using DharmaFECT (DF4) or ELP-L nanoparticle for 16 h. SKOV-3 GL3 cells were plated at a density of 2,000 cells per well of a 24 well plate and incubated for 16 hours before the treated PBMC were added at a cell density of 20,000 per well. Luciferase activity of SK-OV-3 GL3 cells was measured after 4 days of co-culture. (FIG. 3, Graph A).

Using luciferase expression as a surrogate, these studies demonstrated that condensed isRNA duplexes were able to reduce cell viability in SKOV-3 cells co-cultured with PBMCs. These viability decreases indicated that the isRNA oligonucleotides delivered using ELP-L nanoparticles were capable of activating PBMCs that yield species capable of reducing or eliminating viability of the co-cultured tumor cells.

Figure 3:
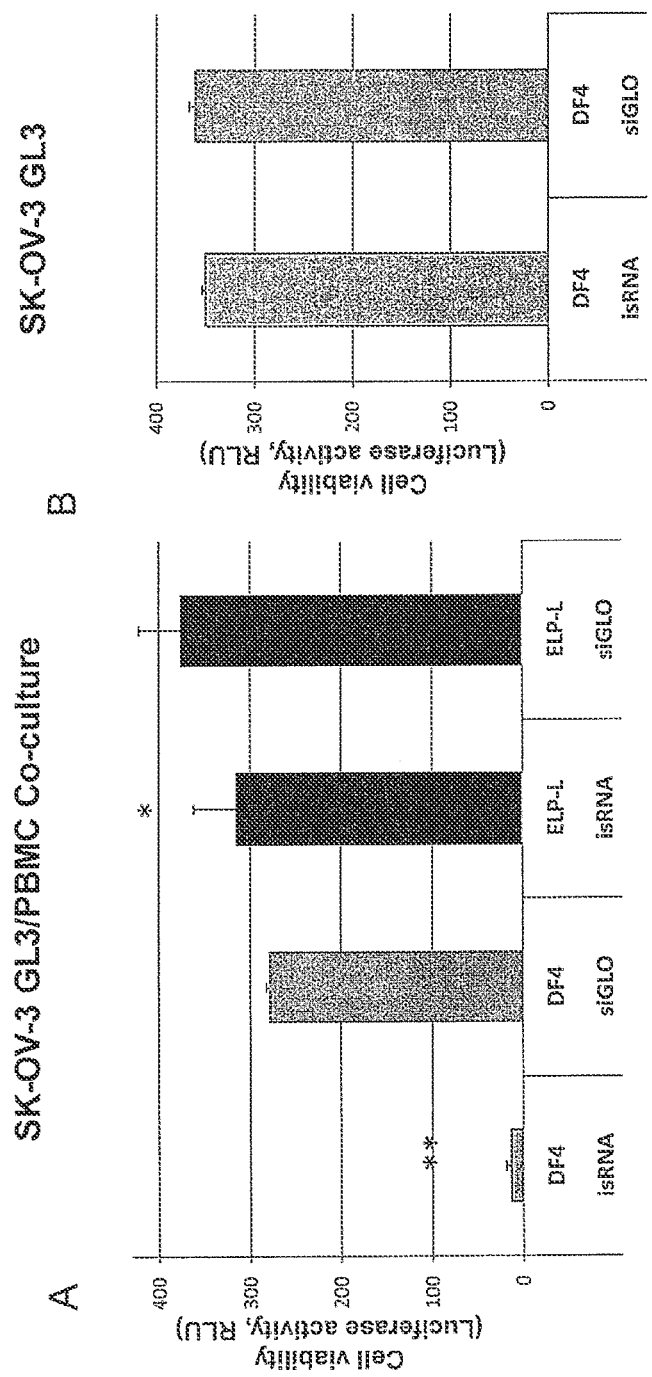
FIG. 3 depicts viability of SKOV-3 GL3 cells (an ovarian cancer cell line stably expressing luciferase) co-cultured with peripheral blood mononuclear cells (PBMC) after treatment with isRNA or siGLO complexed with either DF4 or ELP-L. Luciferase activity (RLU; relative light units) of SK-OV-3 GL3 cells was measured 4 days after adding PBMC to the SKOV-3 GL3 cells (co-culture) (FIG. 3, Graph A). As a control, luciferase activity of SK-OV-3 GL3 cells was measured under the same conditions but with no addition of PBMC cells (FIG. 3, Graph B). * Significance between mean viability of siGLO and isRNA treated co-cultures was determined by T-test at 4 day time-point with $P=0.05$. ** Significance between mean viability of siGLO and isRNA treated co-cultures was determined by T-test at 4 day time-point with $P=0.0005$.

As shown in FIG. 3 (Graph A), the SK-OV-3 GL-3 cells that were co-cultured with PBMCs exposed to 50 nM isRNA duplexes for 16 hours expressed significantly lower amounts of luciferase than cells exposed to control siGLO siRNA. Specifically, SK-OV-3 GL-3 cells that were co-cultured with PBMCs that were exposed to isRNA:DF4 complexes produced 95% less RLU than SK-OV-3 GL-3 cells that were co-cultured with PBMCs that were exposed to siGLO:DF4 complexes, and cells exposed to isRNA:ELP-L complexes produced 30% less RLU than cells exposed to siGLO:ELP-L complexes. As a control, there was no effect on luciferase activity in SKOV-3 GL3 cells exposed to 50 nM isRNA:DF4 or 50 nM siGLO:DF4 duplexes without PBMC co-culture (FIG. 3, Graph B).

Example 3: Effect of isRNA on Human Pancreatic Cancer Cells Activated by PBMCs

The experiments of the previous example (Example 2) were repeated using a human pancreatic cancer cell line (Panc1). A Panc1 cell line that stably expresses firefly luciferase was generated from the pGL-3 plasmid (Promega) using conventional molecular biology techniques, and was thus referred to herein as Panc1 GL3. The time course of the isRNA administration and co-culture of the PBMCs was identical to that used in Example 2. Luciferase expression from the Panc1 GL3 cell line was used as a surrogate for cell viability in the following studies performed substantially as set forth above in Example 2.

Figure 4:
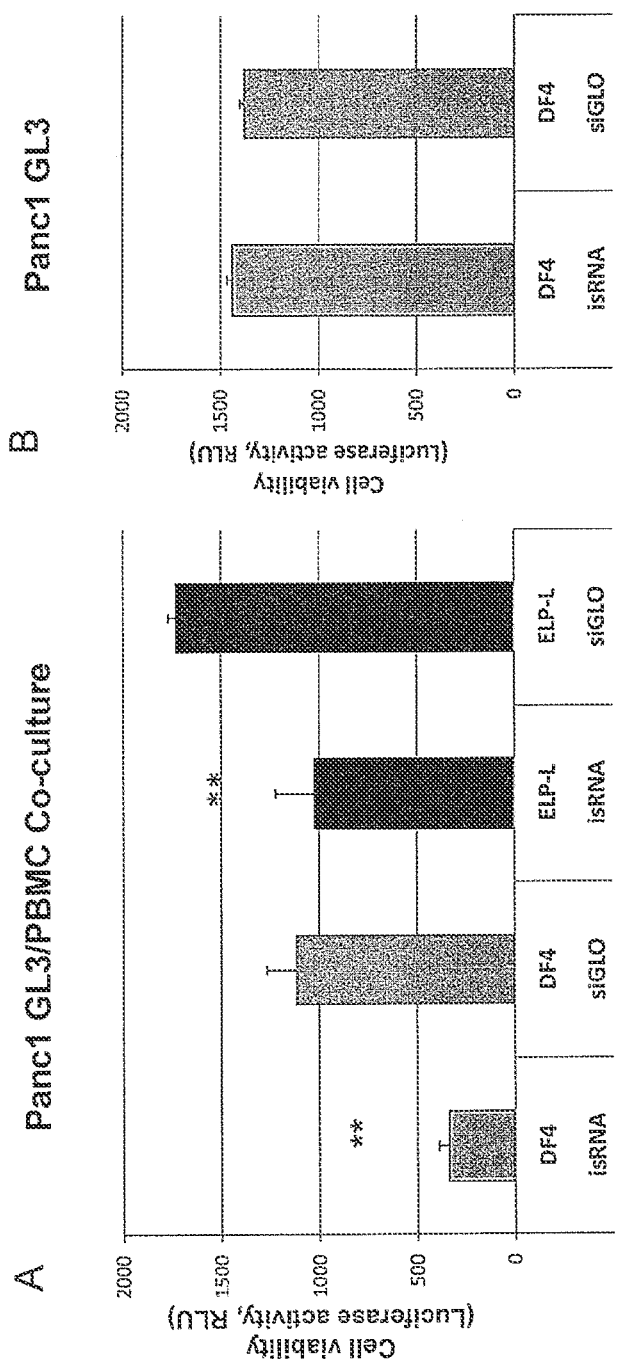
FIG. 4 depicts viability of Panc1 GL3 cells (a pancreatic cancer cell line stably expressing luciferase) co-cultured with peripheral blood mononuclear cells (PBMC) after treatment with isRNA or siGLO complexed with either DF4 or ELP-L. Luciferase activity (RLU; relative light units) of Panc1 GL3 cells was measured 4 days after adding PBMC to the Panc1 GL3 cells (co-culture) (FIG. 4, Graph A). As a control, luciferase activity of Panc1 GL3 cells was measured under the same conditions but without addition of PBMC cells (FIG. 4, Graph B).

As shown in FIG. 4 (Graph A), the Panc1 GL-3 cells that were co-cultured with PBMCs that were exposed to 50 nM isRNA duplexes for 16 hours expressed significantly lower amounts of luciferase than Panc1 GL-3 cells that were co-cultured with PBMCs that were exposed to 50 nM control siGLO siRNA. As a control, there was no effect on luciferase expression in Panc1 GL3 cells exposed to 50 nM isRNA:DF4 or 50 nM siGLO:DF4 duplexes without PBMC co-culture. (FIG. 4, Graph B).

These results confirmed the generality of the tumor cell killing capacity induced in PBMCs after treatment with isRNA reagents as provided herein and that the antitumor effect shown in Example 2 was not limited only to human ovarian cancer cells.

Example 4: Measuring Expression of Cytokines in Treated PBMCs by RT-PCR

PBMCs produce and release cytokines that activate natural killer (NK), dendritic, and monocyte cells and cytotoxic T-cells of the innate immune system to remove cancer cells from a subject. To evaluate whether isRNA complexes activate PBMCs to produce cytokines, RT-PCR was performed on co-cultured cells to assess production of representative cytokines that respond to TLR activation. IL-6 and interferon alpha (INF-α) were selected as representative cytokines for RT-PCR analysis.

RNA from co-cultured PBMCs treated with isRNA complexes as set forth in Examples 2 and 3 was purified using the GeneJET RNA Purification Kit (Fermentas) and quantified. Approximately 100 ng of RNA from each sample was used for first strand cDNA synthesis using the Verso cDNA Synthesis Kit (Thermo Fisher Scientific Inc., MA). A small portion (approx. ⅕s of the sample) of first strand cDNA was used for PCR with forward and reverse primers amplifying IL-6 or INF-α using DreamTaq Green Mix (Fermentas). Expression of β-Actin was also amplified and measured as a normalization control. RT-PCR as described was also performed on PBMCs treated with siGLO as an additional control. The primers used for PCR amplification of IL-6, INF-α, and β-Actin cDNA are listed below in Table 3.

TABLE 3

Sequences used for RT-PCR measurement of cytokine expression

| Primer | Sequence (5'-3') | SEQ ID NO. | PCR product (bp) | Source of sequence |
|---|---|---|---|---|
| IL-6 F | GAACTCCTTCTCCACAAGCG | 7 | 315 | NCBI Accession: NM_000600.3 |
| IL-6 R | AATCCAGATTGGAAGCATCC | 8 | | |
| INF-α F | TTCAGCACAGAGGACTCATC | 9 | 220 | NCBI Accession: NM_021268.2 |
| INF-α R | AGGCACAAGGGCTGTATTTC | 10 | | |
| β-Actin F | GGGAAATCGTGCGTGACATTAAG | 11 | 275 | GenBank Accession: AK223055 |
| β-Actin R | TGTGTTGGCGTACAGGTCTTTG | 12 | | |

Figure 5:
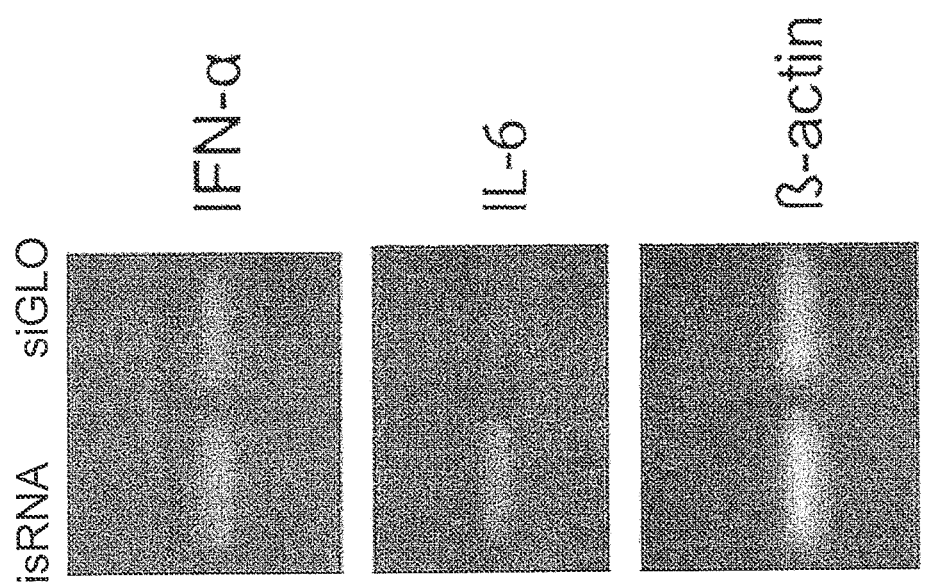
FIG. 5 depicts reverse transcription-polymerase chain reaction (RT-PCR) experiments using PBMCs treated with either isRNA or siGLO complexes. RNA was purified from co-cultured SK-OV-3 GL3/PBMC cells and INF-α and IL-6 expression was measured for each sample. β-actin was measured as a normalization control.

As shown in FIG. 5, increased expression of INF-α and IL-6 mRNA was observed in isRNA-treated PBMCs compared with siGLO-treated PBMCs. These results indicated that isRNA increased cytokine production in PBMCs, which indicate an increased activation of cells of the innate immune system such as NK, dendritic, and monocyte cells and cytotoxic T-cells.

Example 5: Effects of isRNA on Tumor Nodule Size and Number

To test the effects of isRNA in vivo, athymic Balb/c mice were injected with SKOV-3 GL3 cells (human ovarian cancer cells that express luciferase) and tumors were allowed to grow for 4 weeks. Mice were then dosed twice per week for 4 weeks with vehicle (5% dextrose) or isRNA duplex condensed with ELP-L at a concentration of 2 mg/kg (~0.4 mg per dose) or 10 mg/kg (~1.2 mg per dose). isRNA:ELP-L complexes were prepared as described above.

Figure 6:
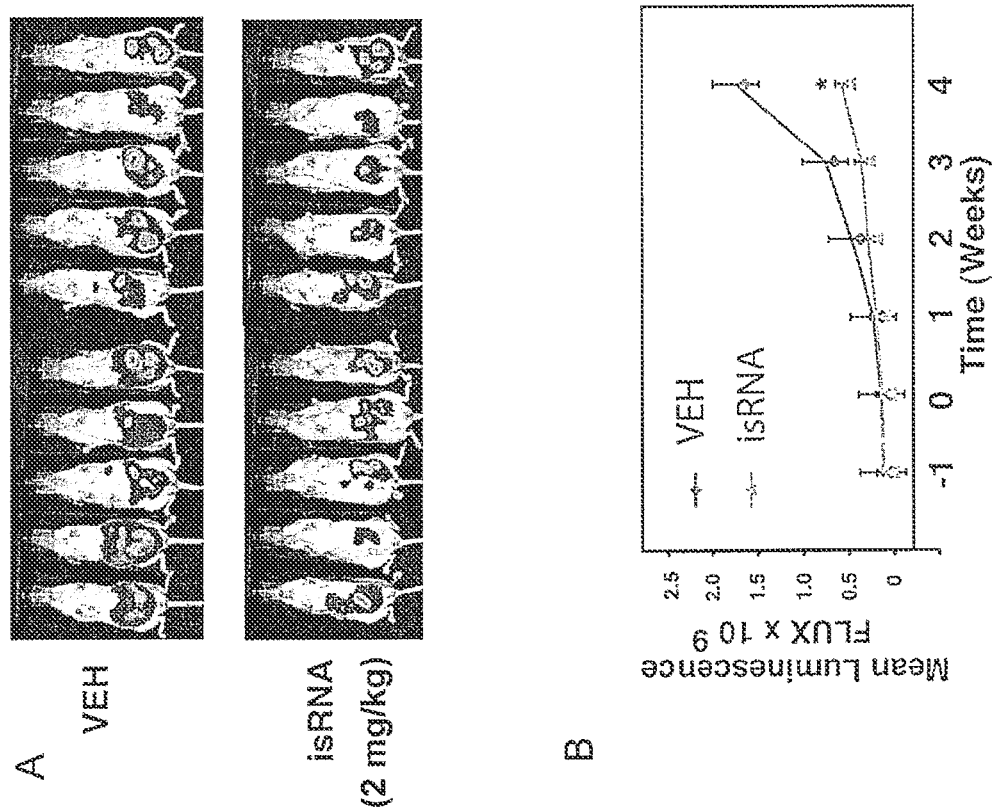
FIG. 6 demonstrates efficacy of isRNA:ELP-L nanocomplexes on growth of ovarian tumors in a mouse model. Growth of tumors in athymic mice (Balb/c) developed from injected SK-OV-3 GL3 cells was measured by bioluminescence in mice dosed twice a week for 4 weeks with vehicle (VEH; 5% dextrose), or 2 mg/kg or 10 mg/kg isRNA/ELP-L (isRNA, n=10). Part A shows the bioluminescence of tumors in viable mice at day 28 of the 2 mg/kg dosing protocol. Part B shows a graph of mean bioluminescence every 7 days for the 2 mg/kg dosing protocol. Data shown are mean of n=10 for each point. * Significance between VEH and isRNA was determined by T-test at the 28 day time-point with $P=0.005$. ** Significance between VEH and isRNA was determined by T-test at the 28 day time-point with $P=0.001$.

As shown in FIG. 6 (Part A), luciferase luminescence was measured in live mice. The bioluminescence was quantified and showed a greater than 50% decrease in bioluminescence following the last dose (FIG. 6, Part B).

Figure 7:
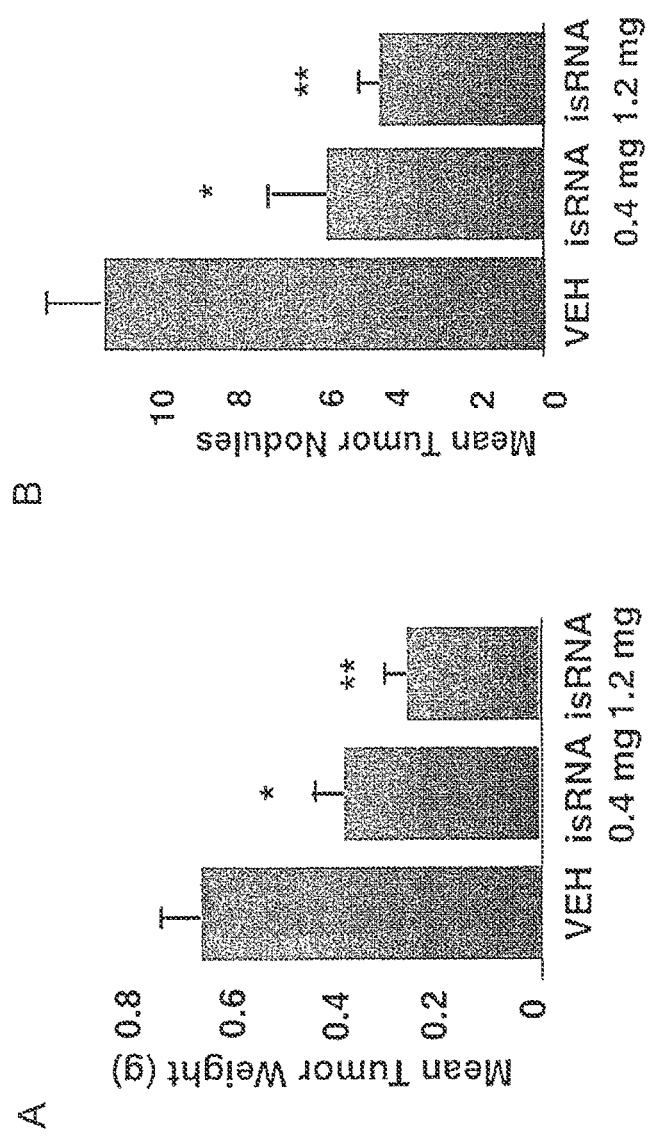
FIG. 7 depicts the weights (Graph A) and number (Graph B) of tumors excised from mice dosed with vehicle (VEH), 2 mg/kg, or 10 mg/kg isRNA:ELP-L.

Tumors were resected from mice, counted and weighed. The results are shown in Table 4 and FIG. 7. As shown, the weight of tumors (FIG. 7, Graph A) and number of tumor nodules (FIG. 7, Graph B) decreased in a dose-dependent manner. These results indicate that the isRNA duplex condensed with ELP-L, as prepared in Example 1, shows anti-tumor activity in vivo.

TABLE 4

Weight and number of tumor nodules from mice administered with various concentrations of isRNA.

| Dose | Nodule Weight (g) | Nodule Number |
|---|---|---|
| Vehicle | 0.63 | 12 |
| 2 mg/kg | 0.40 | 6 |
| 10 mg/kg | 0.23 | 4 |

Example 6: Measuring Expression of Cytokines in Mice after Treatment of Tumors with isRNA Duplexes To determine whether isRNA duplexes can activate the innate immune response when administered to mice, RT-PCR was used to measure expression of IL-6 and INF-α in tumors resected from mice treated with isRNA duplexes at 10 mg/ml. Expression of IL-6 and INF-α in tumors resected from mice dosed with vehicle (5% dextrose) were also measured as a control. RT-PCR was performed as described previously in Example 44.

Figure 8:
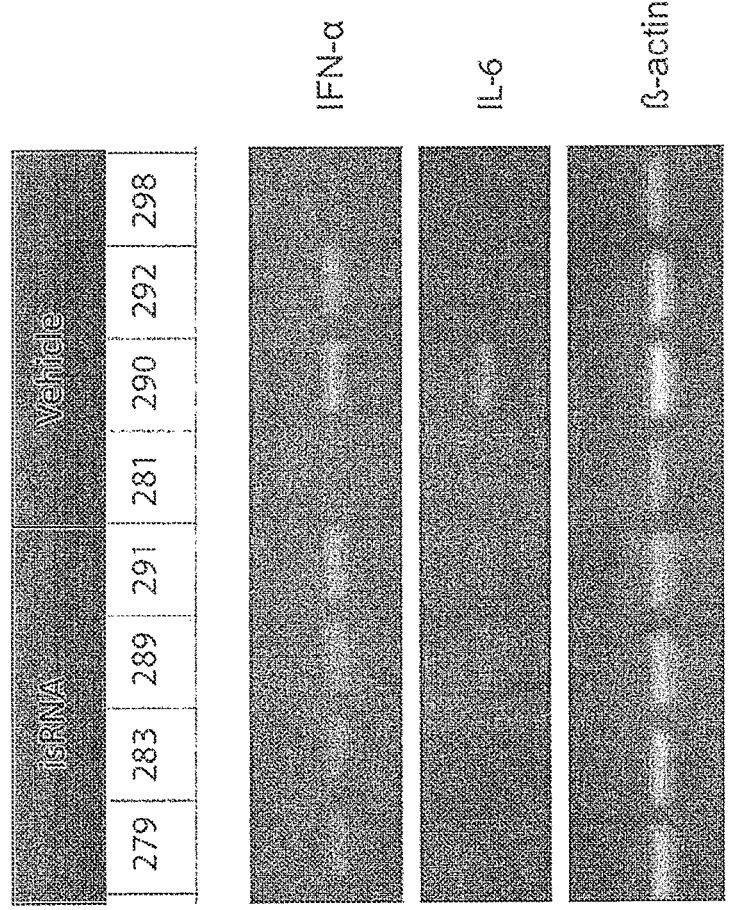
FIG. 8 shows RT-PCR of cytokine expression from mouse tumor samples treated with isRNA:ELP-L or 5% dextrose (vehicle). Tumor samples were excised from mice at 28 days post-injection and expression of INF-α and IL-6 was measured for each sample. R-actin was measured as a normalization control.

As shown in FIG. 8, the mice that received the dosing regimen of isRNA duplexes at 10 mg/ml showed increased expression of INF-α. No significant difference in IL-6 expression between the two groups was observed in this particular experiment.

Example 7: Assessment of Liver and Kidney Damage in Mice Receiving isRNA Treatment Assessment of liver and kidney damage in the mice dosed with isRNA and vehicle was performed by measuring conventional biomarkers of liver and kidney function. The results are shown below in Table 5. Mice that received the isRNA dosing regimen at 10 mg/kg showed an average AST increase of about 67% and an average ALT increase of about 128% over mice dosed with vehicle (see Table 5, columns 1-2). Despite the increase, the AST and ALT numbers for mice dosed at 10 mg/kg isRNA fell within normal acceptable range. The ratio of blood urea nitrogen (BUN) to creatinine did not show any significant increase between the isRNA and vehicle-dosed groups (see Table 5, columns 3-5). This lack of liver and kidney toxicity indicated that the isRNA was successfully delivered to tumor cells, but did not affecting normal healthy cells. These results are consistent with delivery of the isRNA using the ELP-L nanoparticle being a safe and effective anti-tumor agent.

TABLE 5

Blood chemistry in mice after 28 day dosing regimen.

| Treatment | AST (U/L) | ALT (U/L) | BUN (mg/dL) | Creatinine (mg/dL) | BUN/ Creatinine |
|---|---|---|---|---|---|
| isRNA | 263 ± 69 | 178 ± 58 | 17 ± 0.5 | 0.2 ± 0.01 | 78 ± 4 |
| VEH | 157 ± 25 | 78 ± 12 | 15 ± 0.4 | 0.3 ± 0.02 | 62 ± 4 |

All results are shown as mean ± SEM.

Having described the invention in detail and by reference to specific embodiments thereof, it will be apparent that modifications and variations are possible without departing from the scope of the invention defined in the appended claims. More specifically, although some aspects of the invention are identified herein as particularly advantageous, it is contemplated that the invention is not necessarily limited to these particular aspects of the invention.

REFERENCES CITED

Alexopoulou, L., A. C. Holt, et al. (2001). "Recognition of double-stranded RNA and activation of NF-kappaB by Toll-like receptor 3." *Nature* 413(6857): 732-738.

Bridge, A. J., S. Pebernard, et al. (2003). "Induction of an interferon response by RNAi vectors in mammalian cells." *Nat Genet* 34(3): 263-264.

Cekaite, L., G. Furset, et al. (2007). "Gene expression analysis in blood cells in response to unmodified and 2'-modified siRNAs reveals TLR-dependent and independent effects." *J Mol Biol* 365(1): 90-108.

Christensen, S. R., J. Shupe, et al. (2006). "Toll-like receptor 7 and TLR9 dictate autoantibody specificity and have opposing inflammatory and regulatory roles in a murine model of lupus." *Immunity* 25(3): 417-428.

Diebold, S. S., T. Kaisho, et al. (2004). "Innate antiviral responses by means of TLR7-mediated recognition of single-stranded RNA." *Science* 303(5663): 1529-1531.

Elbashir, S. M., J. Harborth, et al. (2001). "Duplexes of 21-nucleotide RNAs mediate RNA interference in cultured mammalian cells." *Nature* 411(6836): 494-498.

Fire, A., S. Xu, et al. (1998). "Potent and specific genetic interference by double-stranded RNA in *Caenorhabditis elegans*." *Nature* 391(6669): 806-811.

Heil, F., H. Hemmi, et al. (2004). "Species-specific recognition of single-stranded RNA via toll-like receptor 7 and 8." *Science* 303(5663): 1526-1529.

Hornung, V., M. Guenthner-Biller, et al. (2005). "Sequence-specific potent induction of IFN-alpha by short interfering RNA in plasmacytoid dendritic cells through TLR7." *Nat Med* 11(3): 263-270.

Jackson, A. L., J. Burchard, et al. (2006). "Widespread siRNA "off-target" transcript silencing mediated by seed region sequence complementarity." *RNA* 12(7): 1179-1187.

Janssens, S. and R. Beyaert (2003). "Role of Toll-like receptors in pathogen recognition." *Clin Microbiol Rev* 16(4): 637-646.

Judge, A. D., G. Bola, et al. (2006). "Design of noninflammatory synthetic siRNA mediating potent gene silencing in vivo." *Mol Ther* 13(3): 494-505.

Judge, A. D., V. Sood, et al. (2005). "Sequence-dependent stimulation of the mammalian innate immune response by synthetic siRNA." *Nat Biotechnol* 23(4): 457-462.

Kariko, K., P. Bhuyan, et al. (2004). "Exogenous siRNA mediates sequence-independent gene suppression by signaling through toll-like receptor 3." *Cells Tissues Organs* 177(3): 132-138.

Kawai, T. and S. Akira (2006). "Innate immune recognition of viral infection." *Nat Immunol* 7(2): 131-137.

Kim, D. H., M. Longo, et al. (2004). "Interferon induction by siRNAs and ssRNAs synthesized by phage polymerase." *Nat Biotechnol* 22(3): 321-325.

Kim, D. H. and J. J. Rossi (2007). "Strategies for silencing human disease using RNA interference." *Nat Rev Genet* 8(3): 173-184.

Kleinman, M. E., K. Yamada, et al. (2008). "Sequence- and target-independent angiogenesis suppression by siRNA via TLR3." *Nature* 452(7187): 591-597.

Kumar, A., J. Hague, et al. (1994). "Double-stranded RNA-dependent protein kinase activates transcription factor NF-kappa B by phosphorylating I kappa B." *Proc Natl Acad Sci USA* 91(14): 6288-6292.

Lau, C. M., C. Broughton, et al. (2005). "RNA-associated autoantigens activate B cells by combined B cell antigen receptor/Toll-like receptor 7 engagement." *J Exp Med* 202(9): 1171-1177.

Lee, J., T. H. Chuang, et al. (2003). "Molecular basis for the immunostimulatory activity of guanine nucleoside analogs: activation of Toll-like receptor 7." *Proc Natl Acad Sci USA* 100(11): 6646-6651.

Lund, J. M., L. Alexopoulou, et al. (2004). "Recognition of single-stranded RNA viruses by Toll-like receptor 7." *Proc Natl Acad Sci USA* 101(15): 5598-5603.

Manche, L., S. R. Green, et al. (1992). "Interactions between double-stranded RNA regulators and the protein kinase DAI" *Mol Cell Biol* 12(11): 5238-5248.

Matsumoto, M., K. Funami, et al. (2004). "Toll-like receptor 3: a link between toll-like receptor, interferon and viruses." *Microbiol Immunol* 48(3): 147-154.

Michels, S., U. Schmidt-Erfurth, et al. (2006). "Promising new treatments for neovascular age-related macular degeneration." *Expert Opin Investig Drugs* 15(7): 779-793.

Pardoll, D. M. (2012). "The blockade of immune checkpoints in cancer immunotherapy." *Nat Rev Cancer* 12(4): 252-264.

Pisitkun, P., J. A. Deane, et al. (2006). "Autoreactive B cell responses to RNA-related antigens due to TLR7 gene duplication." *Science* 312(5780): 1669-1672.

Poeck, H., R. Besch, et al. (2008). "5'-Triphosphate-siRNA: turning gene silencing and Rig-I activation against melanoma." *Nat Med* 14(11): 1256-1263.

Robbins, M., A. Judge, et al. (2008). "Misinterpreting the therapeutic effects of small interfering RNA caused by immune stimulation." *Hum Gene Ther* 19(10): 991-999.

Robbins, M., A. Judge, et al. (2007). "2'-O-methyl-modified RNAs act as TLR7 antagonists." *Mol Ther* 15(9): 1663-1669.

Rossi, J. J. (2009). "Innate immunity confounds the clinical efficacy of small interfering RNAs (siRNAs)." *Gene Ther* 16(5): 579-580.

Sioud, M. (2005). "Induction of inflammatory cytokines and interferon responses by double-stranded and single-stranded siRNAs is sequence-dependent and requires endosomal localization." *J Mol Biol* 348(5): 1079-1090.

Sledz, C. A. and B. R. Williams (2003). "RNA interference and interferon." *Discov Med* 3(18): 30-31.

Subramanian, S., K. Tus, et al. (2006). "A TIr7 translocation accelerates systemic autoimmunity in murine lupus." *Proc Natl Acad Sci USA* 103(26): 9970-9975.

Swann, J. B. and M. J. Smyth (2007). "Immune surveillance of tumors." *J Clin Invest* 117(5): 1137-1146.

Topalian, S. L., F. S. Hodi, et al. (2012). "Safety, activity, and immune correlates of anti-PD-1 antibody in cancer." *N Engl J Med* 366(26): 2443-2454.

Ulevitch, R. J. (2004). "Therapeutics targeting the innate immune system." *Nat Rev Immunol* 4(7): 512-520.

Vollmer, J., S. Tluk, et al. (2005). "Immune stimulation mediated by autoantigen binding sites within small nuclear RNAs involves Toll-like receptors 7 and 8." *J Exp Med* 202(11): 1575-1585.

Whitmore, M. M., M. J. DeVeer, et al. (2004). "Synergistic activation of innate immunity by double-stranded RNA and CpG DNA promotes enhanced antitumor activity." *Cancer Res* 64(16): 5850-5860.

Williams, B. R. (1999). "PKR; a sentinel kinase for cellular stress." *Oncogene* 18(45): 6112-6120.

Wolchok, J. D., H. Kluger, et al. (2013). "Nivolumab plus ipilimumab in advanced melanoma." *N End J Med* 369 (2): 122-133.

Yoneyama, M., M. Kikuchi, et al. (2004). "The RNA helicase RIG-I has an essential function in double-stranded RNA-induced innate antiviral responses." *Nat Immunol* 5(7): 730-737.

---

What is claimed is:

1. A composition for targeting tumor cells and inhibiting tumor growth by activating a subject's innate immune response, the composition comprising:
   an isolated double stranded oligonucleotide comprising a strand comprising the nucleic sequence of SEQ ID NO: 1 and a strand comprising the nucleic sequence of SEQ ID NO: 2;
   a tumor cell-targeting moiety; and
   a pharmaceutically acceptable salt thereof,
   wherein said oligonucleotide activates a subject's innate immune response through activation of one or more toll-like receptors ("TLRs").

2. The composition of claim 1, wherein said tumor cell-targeting moiety is a protein, a peptide, or an aptamer.

3. The composition of claim 1, wherein said composition further comprises a nanoparticle.

4. The composition of claim 3, wherein said nanoparticle comprises lipids, cyclodextrin, chitosan, carbohydrate polymers, elastin-like polypeptides (ELP), calcium phosphate polymers, or combinations thereof.

5. The composition of claim 3, wherein said nanoparticle is PEGylated.

6. The composition of claim 3, wherein the nanoparticle is ELP-L.

7. The composition of claim 1, wherein the composition is encapsulated in a liposome.

8. The composition of claim 7, wherein the liposome is PEGylated.

9. A pharmaceutical composition comprising:
   the composition of claim 1; and
   a pharmaceutically acceptable carrier, excipient or adjuvant.

10. The pharmaceutical composition of claim 9, further comprising a chemotherapeutic drug or agent.

11. The pharmaceutical composition of claim 9, further comprising an immune checkpoint inhibitor.

12. A method for inhibiting tumor growth, comprising:
    contacting the tumor with the composition of claim 1 in an amount sufficient to inhibit tumor growth.

13. A method for activating a subject's innate immune response specifically in the tumor of the subject, the method comprising:
    obtaining an isolated double stranded oligonucleotide comprising a strand comprising the nucleic sequence of SEQ ID NO: 1 and a strand comprising the nucleic sequence of SEQ ID NO: 2;
    contacting the oligonucleotide with a tumor cell-targeting moiety to form a composition, such that the composition will specifically deliver the oligonucleotide to the tumor in the subject; and
    administering a pharmaceutically effective amount of the composition to the subject, wherein the oligonucleotide within the composition activates a subject's innate immune response by activating one or more TLRs.

14. The method of claim 12 or 13, wherein the tumor is a human bladder tumor, a human breast tumor, a human colon tumor, a human liver tumor, a human lung tumor, a human neuroblastoma tumor, a human ovarian tumor, a human pancreatic tumor, a human prostate tumor, or a human skin tumor.

15. The composition of claim 1, wherein the composition is encapsulated in a nanoparticle.

16. The composition of claim 1, wherein the tumor cell-targeting moiety comprises a peptide that binds L1 cell adhesion molecule (L1CAM).

17. The composition of claim 1, wherein the tumor cell-targeting moiety is the cell targeting domain of ELP-L.

18. A method for reducing the number of tumors disseminated from a primary tumor by contacting the tumor with the composition of claim 1 in an amount sufficient to reduce the number of tumors.

19. The composition of claim 1, wherein at least one activated TLR is TLR-3.

20. The method of claim 13, wherein at least one activated TLR is TLR-3.

* * * * *

SEQUENCE LISTING

```
<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 1
aauucuccga acgugucac                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 2
gugacacguu cggagaauu                                                19

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: modification of the 2' ribose position
```

```
<220> FEATURE:
<221> NAME/KEY: misc_feature
<222> LOCATION: (20)..(20)
<223> OTHER INFORMATION: deoxyribothymidine
<220> FEATURE:
<221> NAME/KEY: misc_feature
<222> LOCATION: (21)..(21)
<223> OTHER INFORMATION: deoxyribothymidine

<400> SEQUENCE: 3
aauucuccga acgugucact t                                                 21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: modification of the 2' ribose position
<220> FEATURE:
<221> NAME/KEY: misc_feature
<222> LOCATION: (20)..(20)
<223> OTHER INFORMATION: deoxyribothymidine
<220> FEATURE:
<221> NAME/KEY: misc_feature
<222> LOCATION: (21)..(21)
<223> OTHER INFORMATION: deoxyribothymidine

<400> SEQUENCE: 4
gugacacguu cggagaauut t                                                 21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: modification of the 2' ribose position
<220> FEATURE:
<221> NAME/KEY: misc_feature
<222> LOCATION: (3)..(3)
<223> OTHER INFORMATION: modification of the 2' ribose position
<220> FEATURE:
<221> NAME/KEY: misc_feature
<222> LOCATION: (4)..(4)
<223> OTHER INFORMATION: modification of the 2' ribose position
<220> FEATURE:
<221> NAME/KEY: misc_feature
<222> LOCATION: (6)..(6)
<223> OTHER INFORMATION: modification of the 2' ribose position
<220> FEATURE:
<221> NAME/KEY: misc_feature
<222> LOCATION: (9)..(9)
<223> OTHER INFORMATION: modification of the 2' ribose position
<220> FEATURE:
<221> NAME/KEY: misc_feature
<222> LOCATION: (13)..(13)
<223> OTHER INFORMATION: modification of the 2' ribose position
<220> FEATURE:
<221> NAME/KEY: misc_feature
<222> LOCATION: (14)..(14)
<223> OTHER INFORMATION: modification of the 2' ribose position
<220> FEATURE:
<221> NAME/KEY: misc_feature
<222> LOCATION: (15)..(15)
<223> OTHER INFORMATION: modification of the 2' ribose position
```

```
<220> FEATURE:
<221> NAME/KEY: misc_feature
<222> LOCATION: (16)..(16)
<223> OTHER INFORMATION: modification of the 2' ribose position
<220> FEATURE:
<221> NAME/KEY: misc_feature
<222> LOCATION: (20)..(20)
<223> OTHER INFORMATION: deoxyribothymidine
<220> FEATURE:
<221> NAME/KEY: misc_feature
<222> LOCATION: (21)..(21)
<223> OTHER INFORMATION: deoxyribothymidine

<400> SEQUENCE: 5
aauucuccga acgugucact t                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: modification of the 2' ribose position
<220> FEATURE:
<221> NAME/KEY: misc_feature
<222> LOCATION: (2)..(2)
<223> OTHER INFORMATION: modification of the 2' ribose position
<220> FEATURE:
<221> NAME/KEY: misc_feature
<222> LOCATION: (3)..(3)
<223> OTHER INFORMATION: modification of the 2' ribose position
<220> FEATURE:
<221> NAME/KEY: misc_feature
<222> LOCATION: (8)..(8)
<223> OTHER INFORMATION: modification of the 2' ribose position
<220> FEATURE:
<221> NAME/KEY: misc_feature
<222> LOCATION: (9)..(9)
<223> OTHER INFORMATION: modification of the 2' ribose position
<220> FEATURE:
<221> NAME/KEY: misc_feature
<222> LOCATION: (10)..(10)
<223> OTHER INFORMATION: modification of the 2' ribose position
<220> FEATURE:
<221> NAME/KEY: misc_feature
<222> LOCATION: (12)..(12)
<223> OTHER INFORMATION: modification of the 2' ribose position
<220> FEATURE:
<221> NAME/KEY: misc_feature
<222> LOCATION: (13)..(13)
<223> OTHER INFORMATION: modification of the 2' ribose position
<220> FEATURE:
<221> NAME/KEY: misc_feature
<222> LOCATION: (15)..(15)
<223> OTHER INFORMATION: modification of the 2' ribose position
<220> FEATURE:
<221> NAME/KEY: misc_feature
<222> LOCATION: (18)..(18)
<223> OTHER INFORMATION: modification of the 2' ribose position
<220> FEATURE:
<221> NAME/KEY: misc_feature
<222> LOCATION: (19)..(19)
<223> OTHER INFORMATION: modification of the 2' ribose position
<220> FEATURE:
<221> NAME/KEY: misc_feature
<222> LOCATION: (20)..(20)
<223> OTHER INFORMATION: deoxyribothymidine
<220> FEATURE:
<221> NAME/KEY: misc_feature
<222> LOCATION: (21)..(21)
<223> OTHER INFORMATION: deoxyribothymidine
```

```
<400> SEQUENCE: 6
gugacacguu cggagaauut t                                              21

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
gaactccttc tccacaagcg                                                20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
aatccagatt ggaagcatcc                                                20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ttcagcacag aggactcatc                                                20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
aggcacaagg gctgtatttc                                                20

<210> SEQ ID NO 11
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 11
gggaaatcgt gcgtgacatt aag                                            23

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 12
tgtgttggcg tacaggtctt tg                                             22
```